United States Patent [19]

Triplett

[11] Patent Number: 5,908,758

[45] Date of Patent: Jun. 1, 1999

[54] MICROORGANISMS

[75] Inventor: Eric W. Triplett, Madison, Wis.

[73] Assignee: Wisconsin Alumni Research Foundation, Madison, Wis.

[21] Appl. No.: 08/879,128

[22] Filed: Jun. 19, 1997

[51] Int. Cl.[6] .............................. C12Q 1/24; C12Q 1/00; C12Q 1/68; C12N 15/11

[52] U.S. Cl. .................................. 435/30; 435/4; 435/6; 435/34; 435/91.2; 435/252.4; 435/252.7; 435/252.34; 435/252.35; 536/23.1; 536/24.3; 536/24.5

[58] Field of Search ................................ 435/30, 91.2, 6, 435/4, 34, 243, 252.4, 252.7, 252.34, 252.35; 536/23.1, 24.3, 24.5

[56] References Cited

PUBLICATIONS

Borneman, James, et al., "Molecular Microbial Diversity in Soils from Eastern Amazonia: Evidence for Unusual Microorganisms and Microbial Population Shifts Associated with Deforestation," *Applied and Environmental Microbiology*, 63(7):1–7 (Jul. 1997).

Borneman, James, et al., "Molecular Microbial Diversity of an Agricultural Soil in Wisconsin," *Aplied and Environmental Microbiology*, 62(6):1935–1943 (Jun. 1996).

McInroy, John A., et al., "Survey of indigenous bacterial endophytes from cotton and sweet corn," *Plant and Soil*, 173(2):337–342 (Jun. 1995).

Morell, Virginia, "Life's Last Domain," *Science*, 273:1043–1045 (Aug. 23, 1996).

Pace, Norman R., "New Perspective on the Natural Microbial World: Molecular Microbial Ecology," *ASM News*, 62(9):463–470 (1996).

Pace, Norman R., "Ribosomal RNA Phylogeny and the Primary Lines of Evolutionary Descent," *Cell*, 45:325–326 (May 9, 1986).

Triplett, Eric W., "Diazotrophic endophytes: progress and prospects for nitrogen fixation in monocots," *Plant and Soil*, 00:1–10 (1995).

Woese, Carl R., "Bacterial Evolution," *Microbiological Reviews*, 51(2):221–271, (Jun. 1987).

Ward et al. (1990) Nature, vol. 345, pp. 63–65.

Nepstad et al. (1994) Nature, vol. 372, pp. 666–669.

*Primary Examiner*—Paula K. Hutzell
*Assistant Examiner*—Khalid Masood
*Attorney, Agent, or Firm*—Quarles & Brady

[57] ABSTRACT

A novel category of microorganisms has been identified from its ribosomal DNA (rDNA) sequence. That sequence, P36, is characteristic of this category of microorganisms, here termed metathermophiles. Methods for isolating samples of metathermophiles using the rDNA sequence are described.

2 Claims, 7 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 938 base pairs
      (B) TYPE: nucleic acid
      (C) STRANDEDNESS: double
      (D) TOPOLOGY: linear    (ii) MOLECULE TYPE: other nucleic acid
      (A) DESCRIPTION: /desc = "rDNA"

(vi) ORIGINAL SOURCE:
      (A) ORGANISM: meththermophile    (xi) SEQUENCE DESCRIPTION: SEQ ID NO:1:

```
TAATACAGAG GTCACAACCG TTATCCGGAT TTATTGGGCG TAAAGCGTTT CGTAGGTGGA      60

TTAGATAGTT ACTCTTCAAA GACCACGGCT CAACCGGGGG AAGGGGAGTA ATACTTCTAG     120

TCTTGAAATA TGGTGGGGTA TCTGGAACTG ATGGTGTAGT AGTGAAATAC GTTGATATCA     180

TCAGGAACTC CAAGGGCGAA GGCAGGATAC TAACCATTTT TTGACACTGA GGAACGACAG     240

CTAGGGGAGC GAAAGGGATT AGAGACCCCT GTAGTCCTAG CCGTAAACTA TGCTCGCTAG     300

GGGTTAGAAT TTATTCTGGC CCCGTAAGCT AACGCGTTAA GCGAGCCGCC TGGGGAGTAC     360

GACCGCAAGG TTAAAACTCA AAGGAATTGA CGGGGACCCG CACAACCAGT GGAGCATGTG     420

GTTTAATTCG AGACGAAACG AAAGACCTCA CCCAGCCTTG ACATACAACC GTTTTAAGCA     480

CCTAAAATAG GAGCCTATCT TTAGAAATAT TGATGGTTGA ACAGGTGTTG CATGGCCGTC     540

GTAAGTTCGT GCCGTAGGGT GTTCCCTTCA GTGGGGTAAC GAACGAAACC CTTATCAAAT     600

ATTAAATATT TATTTGAGAC TTCCTAAATT TATTTTAGGA GGAAGCAGAG GATGACGTCA     660
```

-continued

```
GGTCAGCATG GCCCTTATAG CTGGGGCAAC ACACATACTA CAATGGAGCC GACAAAGGGT       720

TGCCAAAGAC AATCTGGAGC TAATCCCATA AACGGCTTCT CAGTGGGGAT TGGGGGCTGC       780

AACTCGCCCC CATGAACGTG GAATTGGTAG TAATCGCGGA TCAGCATTGC CGCGGTGAAT       840

ACGTTCTCGG GTCTTGTACA CACCGCCCGT CAAGTTAGCA AAGTTGGAGA TACCTTAAAG       900

GCCGCTGTGC GGTCTCAGGT AAATCAGCGA TGAGAATT                               938
```

MICROORGANISMS

CROSS-REFERENCE TO RELATED APPLICATIONS

This invention was made with United States government support awarded by the following agencies EPA Award # CF 822882-01-0; USAID Award# DHR 5453-A-00-9048; USDA AGRICCREE Nos. 94-33120-0433, 94-37305-0767, and Hatch 5201.

Not applicable.

STATEMENT REGARDING FEDERALLY SPONSORED RESEARCH OR DEVELOPMENT

Not applicable.

BACKGROUND OF THE INVENTION

In spite of the extensive amount of research and characterization which has characterized modern biology, only a small portion of the world's microbial species have yet been identified and characterized. In particular, it is well known that the rain forest regions of the planet contain an enormous diversity of flora and fauna including many species which have not yet been recognized by science. Not only have the diversity of life forms at a macrobiological scale been only partly characterized by modern science, very little work has been done in examining the microbiological diversity of the rain forest ecosystems.

The Amazon Basin of South America is the largest tropical rain forest on the planet. There have been estimates that there may be as many as thirty million species of tropical forest arthropods, an estimate which exemplifies the immense biodiversity found in the Amazon Basin. The microbial diversity of the Amazon remains largely uncharacterized. There are numerous factors which lead to this deficiency, not the least of which is the inability of science at present to culture many microorganisms. In soil, comparisons of microbial cell numbers by microscopic counts and enumeration on culture media have shown that using conventional media less than 1% of the native microorganisms can be cultivated. The quantification of this uncharacterized diversity in soils has suggested some startling results.

By measuring the kinetics of denaturation and renaturation of bacteria DNA extracted from soil, one group of scientists have been able to estimate that there are at least 400 different genomes of bacteria contained in a single gram of soil taken from a Norwegian forest. The understanding of the diversity of this microbiological community is thus clearly limited given our present understanding. To address this issue, recent reports have shown that PCR amplification and sequence analysis of rRNA genes can help to provide a phylogenic description of the microorganisms that inhabit the soil.

Ribosomal RNA genes (rDNA) are used to characterize the phylogenic classification of microorganisms. rDNA sequences are used since these particular DNA sequences tend to be highly conserved among closely related organisms. rRNAs or rDNAs are characterized at present as the most useful and most used of the molecular chronometers. By chronometers it is meant to describe a molecule which changes randomly in time and therefore can be used to judge the relatedness of different organisms. The difference in sequence between the rRNA or the rDNA of particular organisms is recognized as a measure of the time at which the two organisms diverged on an evolutionary scale. The use of rRNA sequences as a measurement of molecular chronometer and as a tool for analyzing the phylogenic tree of microorganisms is described in a review article by Woese, *Microbiol. Rev.* 51,2:221–271 (1987), the disclosure of which is hereby incorporated by reference. Within the general realm of ribosomal RNA, a particular portion which has been utilized for phylogenic characterization is the 16S-like rRNA sequences. An early phylogenic tree of the major classifications of life is illustrated by Pace, et al., *Journal Cell*, 45:325–326 (1986).

BRIEF SUMMARY OF THE INVENTION

The present invention is summarized in that a novel group of microorganisms, here termed metathermophiles, has been identified from a soil sample from Amazonian soil. An rDNA sequence diagnostic of this organism, P36, is described in its use to identified to isolate and the organisms of this group are further described. Microorganisms of the group cannot be classified into any of the domains associated with the current phylogenic classification systems for known organisms.

It is an object of the present invention to describe a method for characterizing a novel group of microorganisms and to provide a methodology to isolate those organisms from the environment.

It is an advantage of the present invention in that the identification and study of a novel group of microorganisms provides a rich source for the identification sequencing and utilization of novel enzymes and genes therefor.

Other objects, advantages, and features of the present invention will become apparent from the following specification when taken in conjunction with the accompanying drawings.

DETAILED DESCRIPTION OF THE INVENTION

In essence the present invention is summarized in that an rDNA sequence has been identified and sequenced which is diagnostic of a unique group of microorganisms, here termed metathermophiles. The organisms have been identified here by virtue of the sequence, termed P36, by which those organisms were first identified.

The research described herein began out of an effort to characterize generally microorganisms which could be extracted from Amazonian soil. As described in greater detail below, soil samples were obtained from the Amazon and DNA was extracted from those soils. The rDNA sequences were analyzed for the DNA recovered from the soil samples and the sequences were analyzed for similarities. A phylogenic tree was made from the organisms recovered based on similarities in the rDNA sequences.

A particular sequence, termed P36, was found to have a DNA sequence which was quite unique amongst all those which were studied. Given the relative homology between rDNA sequences from known organisms, it became apparent that this sequence is very unusual and therefore characteristic of a very unusual organism. Primary analysis of the sequence revealed that it would be inappropriate to characterize the organism identified by the presence of this rDNA sequence as a part of any of the existing identified domains of life, either Bacteria, Archaea, or Eukarya.

Figure 1A:
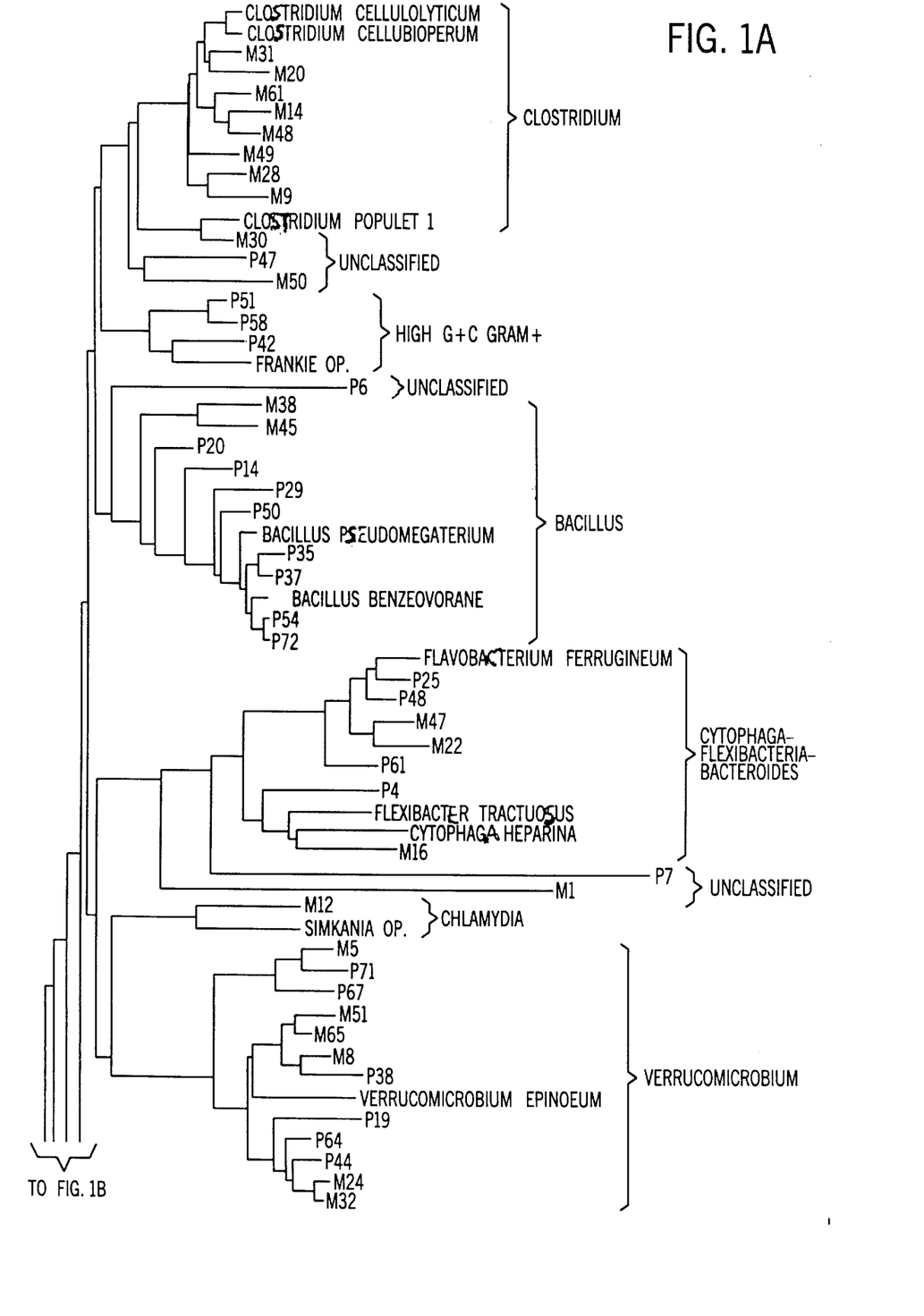
FIGS. 1A–1C constitute an illustration of a phylogenic analysis of the rDNA sequence P36.
Figure 1B:
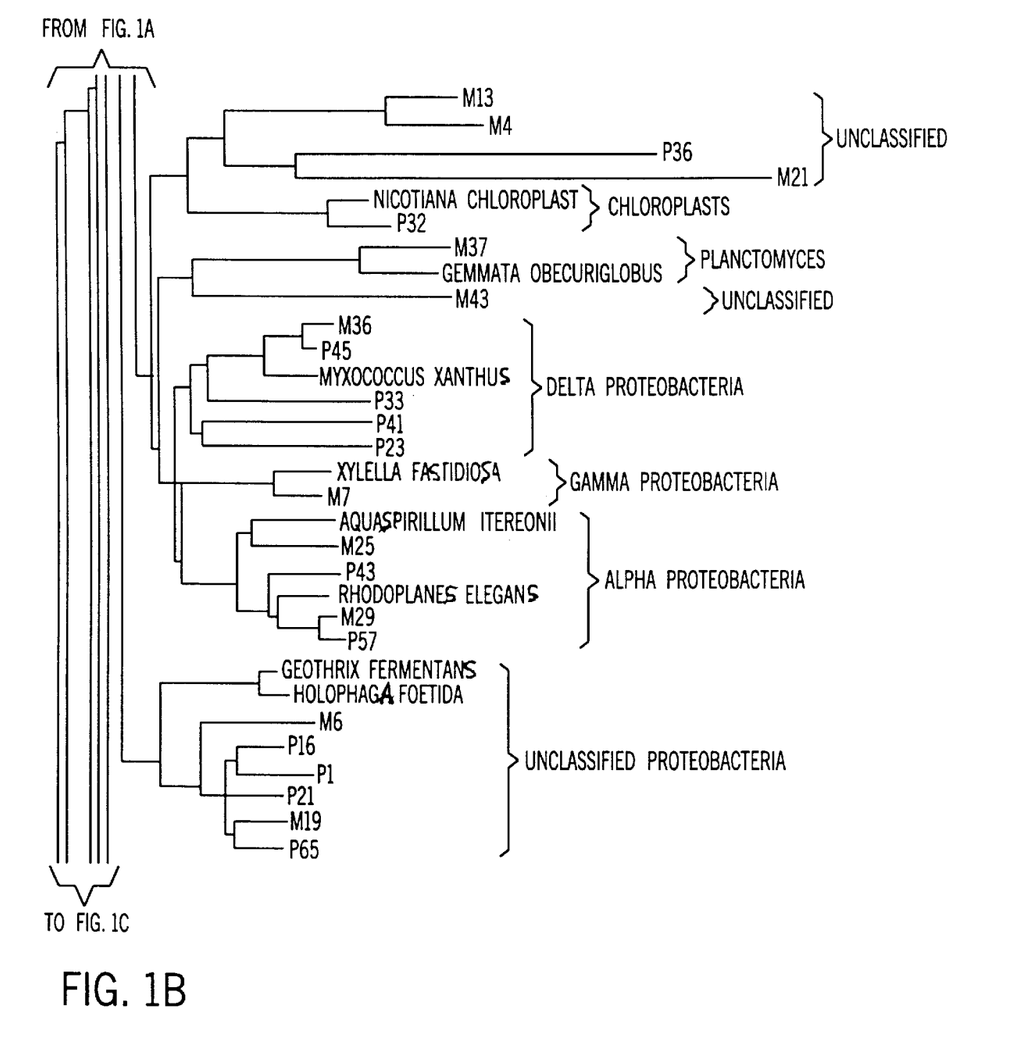
Figure 1C:
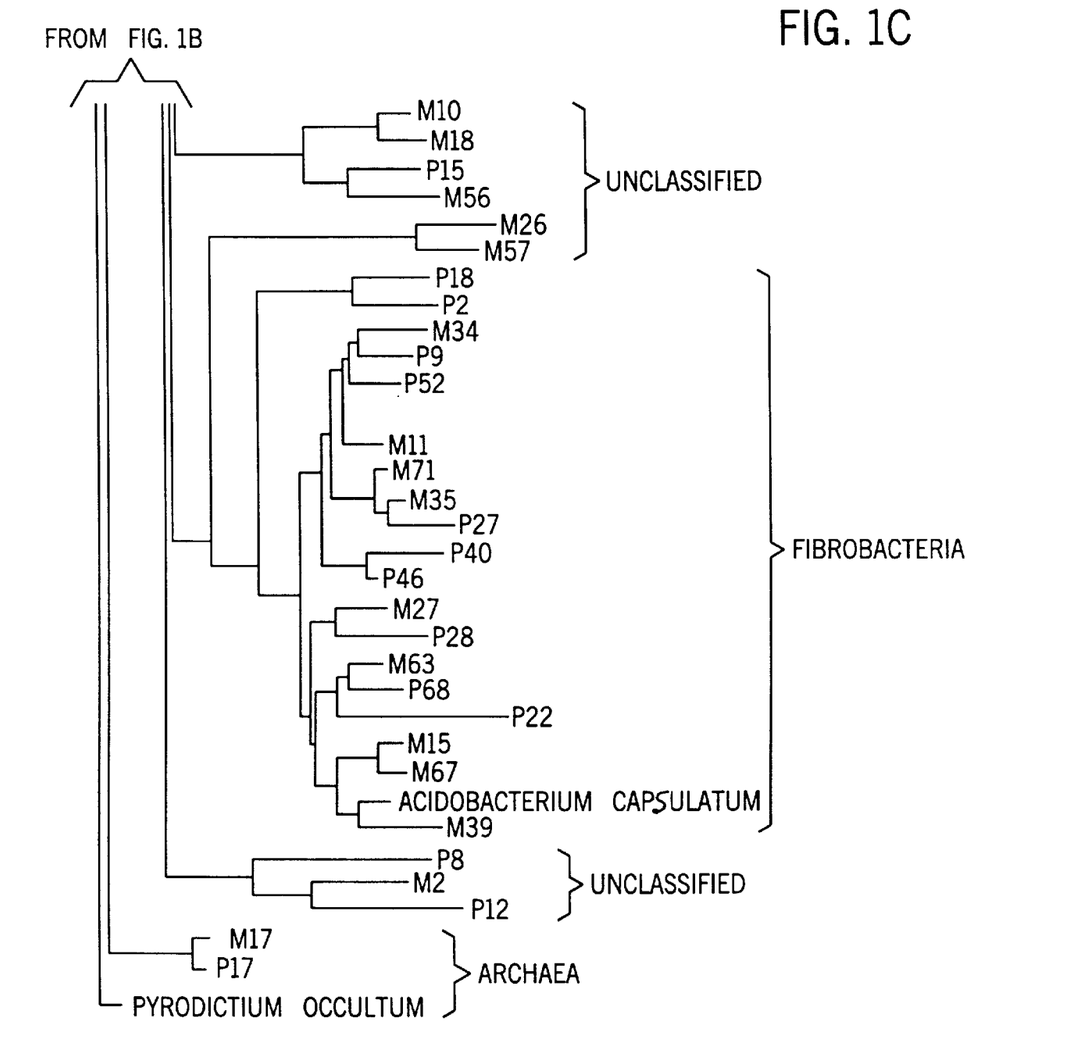

The P36 DNA sequence is set forth below as SEQ ID NO: 1. Using a phylogenic analysis, the diversity illustrated of that sequence compared to other known sequences is illustrated in FIGS. 1A–1C. No duplicate sequences were detected among 100 RNA clones and none have been previously described.

Figure 2A:
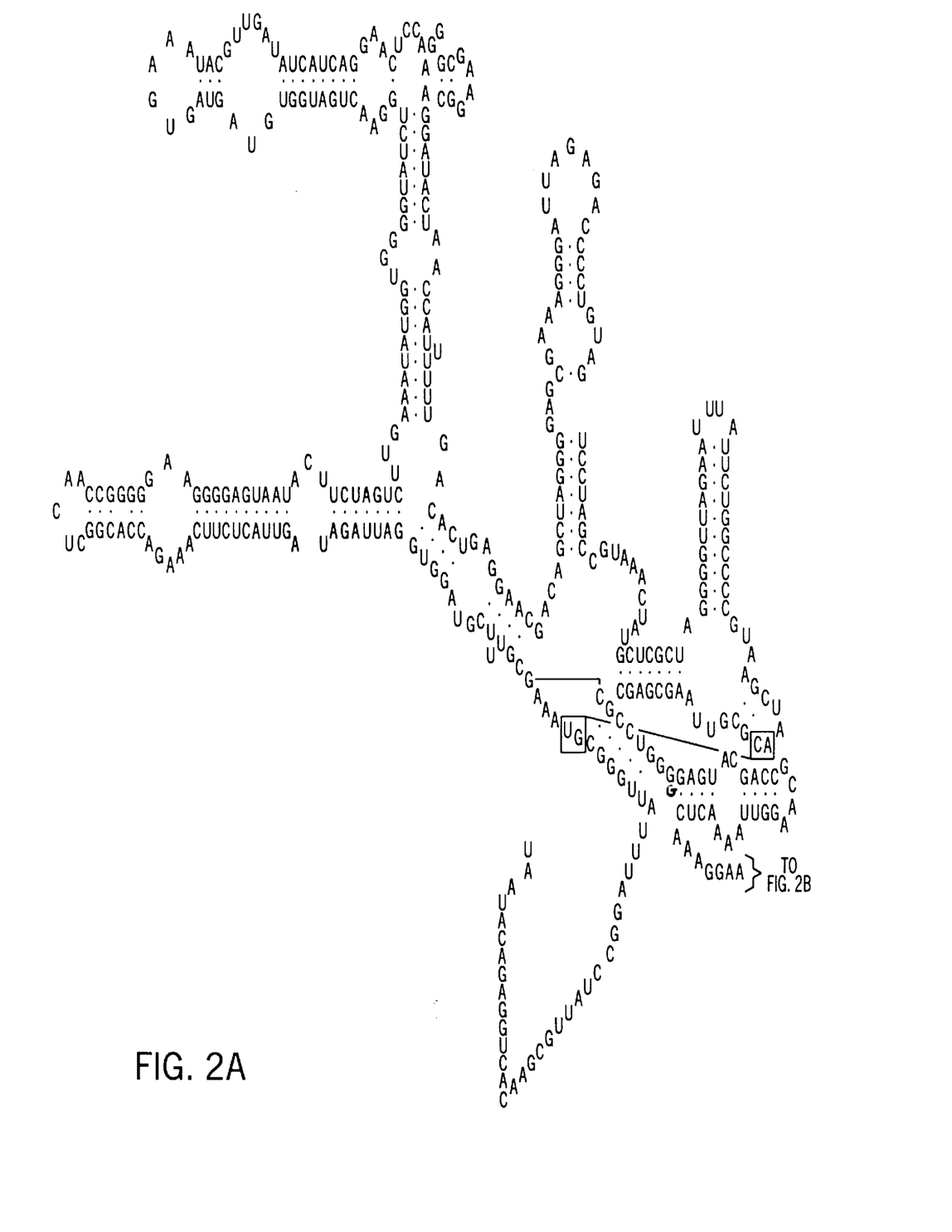
FIGS. 2A–2C constitute an illustration of the derived secondary structure of the P36 rRNA sequence.
Figure 2B:
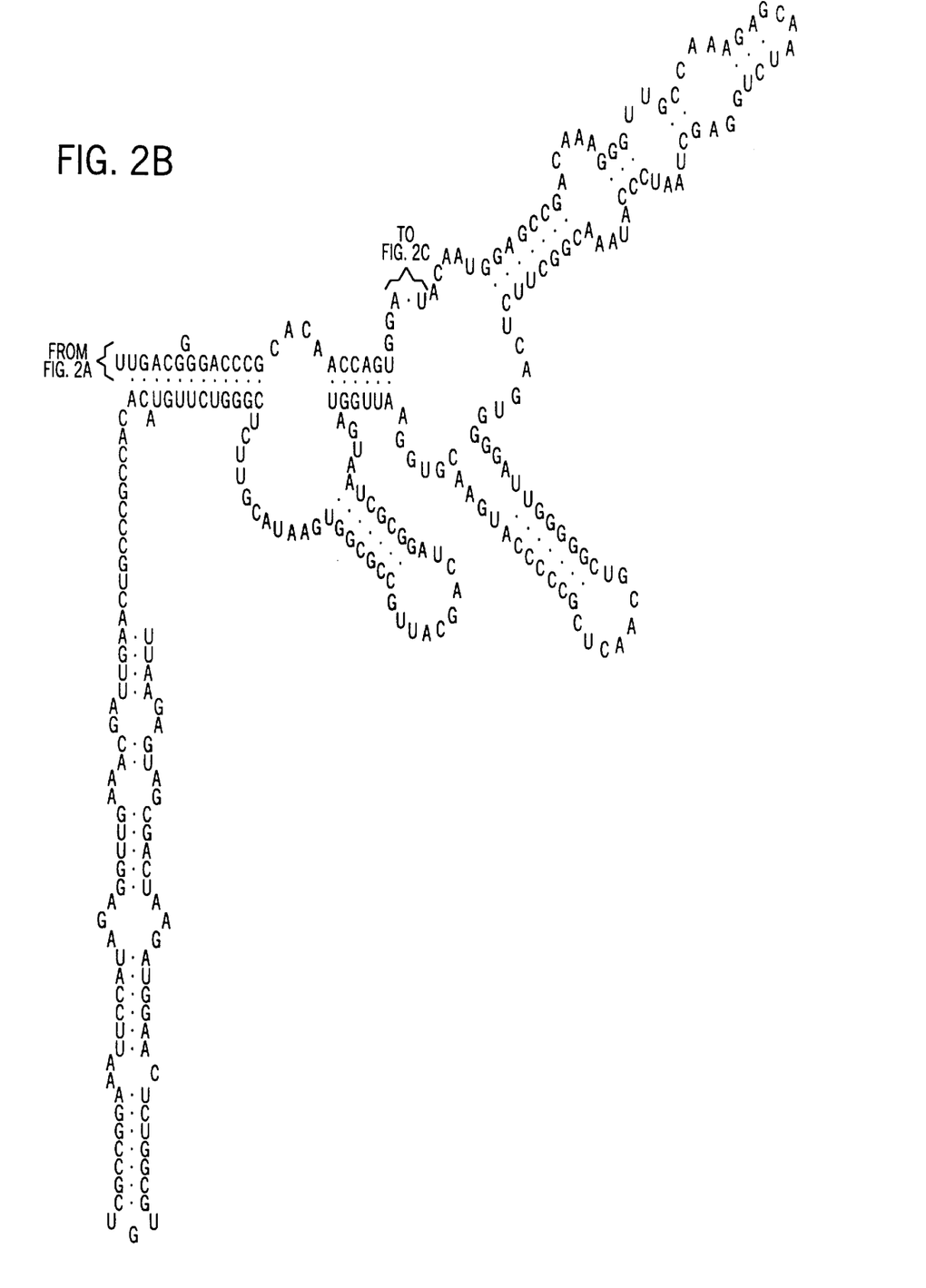
Figure 2C:
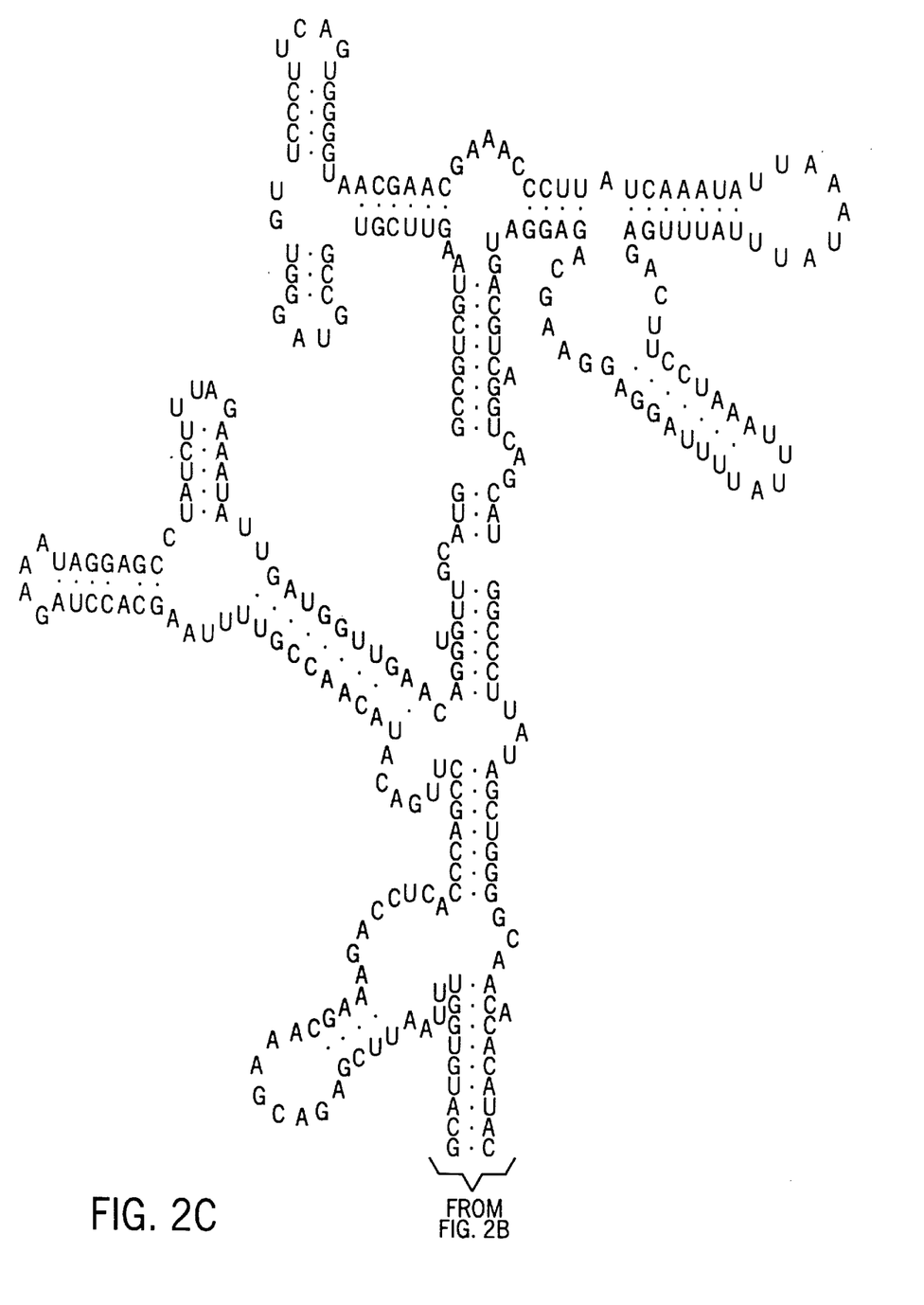

The secondary structure of the P36 sequence is shown in FIGS. 2A–2C. The ability of the P36 sequence to conform to normal rRNA structural constraints, and an analysis of the sequence using the check-chimera program, demonstrates that this sequence is probably not an artifact created by PCR amplification. The P36 DNA sequence appears to have a bacterial origin, because of its bifurcating stem structure at helix 35 as illustrated in FIGS. 2A–2C. This is in contrast to rRNA sequences from Archaea and Eukarya sequences, which possess an unbranched stem-loop structure at this location. However, the P36 sequence also had two distinct structural difference when compared to known bacteria. Helix 41 has a 15 base pair deletion and helix 35 has a 10 base pair insertion when compared to other bacteria, as for example *E. coli*. Other analysis of this sequence suggests that the organism hosting the P36 DNA sequence is quite phylogenically distant from other bacteria as well.

Woese and his colleagues (Woese, supra (1987)) have previously described numerous rRNA nucleotide positions, or signature nucleotides, which define the bacterial kingdoms and their three domains. Attempts to place the P36 sequence into the known bacterial kingdoms using the signatures was not successful. Classification of the P36 sequence into any of the existing domains was also met with limited success since P36 lacks 4 of the 38 bacterial signature nucleotides. This deviation is significant considering a previous study which show that the average divergence from the bacterial consensus was less than 0.4% (Winker and Woese, *System. Appl. Microbiol.* 14:305–310 (1991). In the sequence illustration in FIG. 2 of secondary structure, the numbered arrows designate the positions where the P36 DNA sequence deviates from other bacterial signatures. The nucleotides at arrows numbered 2 through 4 in FIG. 2A–2C are archeal or eukaryotic signatures. The residue indicated at arrow 1 ("A") is an unclassified domain signature. Although the majority of these signatures suggest a bacterial classification, the 11% deviants suggests the curious phylogeny of the sequence which is not typical of bacterial sequences.

Figure 3:
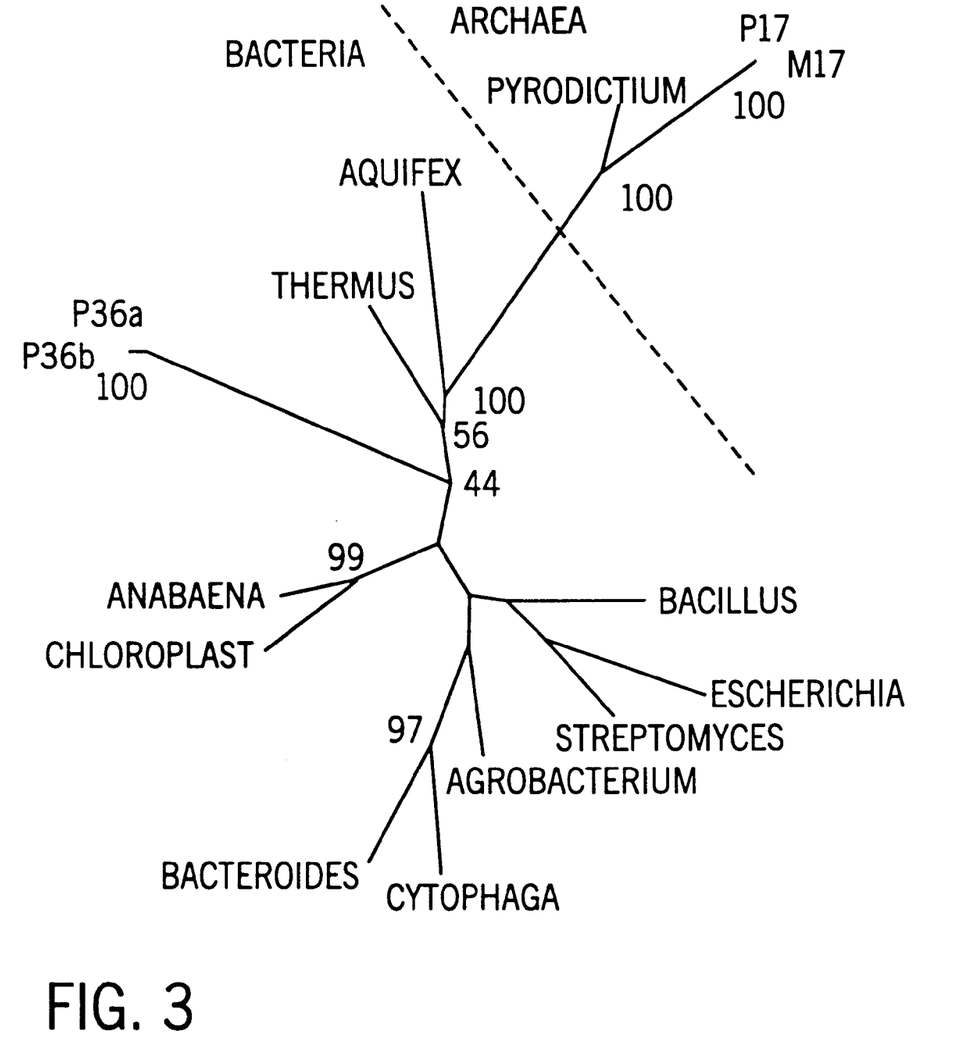
FIG. 3 is an illustration of the deduced phylogenic tree for metathermophile (P36) microorganisms.

The examination of the P36 DNA sequence using maximal likelihood approach tentatively places the P36 DNA into a unique branch between the vast majority of bacteria and the deeply branching predominantly thermophylic bacteria, as illustrated in FIG. 3. It is the relationship to the true thermophylic bacteria that gives use to the designation metathermophilic. This assignment is provisional since the probability of this branching pattern is only 44%. The maximum likelihood analysis also provides a means of visualizing the degree of sequence differentiation between the metathermophilic microorganism and its closest relatives. In fact there are approximately the same number of DNA substitutions between the Archeon, *Pyrodictium occultum* and the bacterium, *Aquifex pyrophilus* as there are between the P36 microorganisms and its closest relatives yet identified.

Methods now exist by which unknown microorganisms in the soil identified only by their rDNA sequences can be isolated and cultured from soil samples. Huber et al., *Nature* 376:57–58 (1995), which is hereby incorporated by reference, describe a method of culturing an organism using only its 16S rRNA sequence. In general, the method uses optical tweezers to trap a single cell that is tagged with a fluorescently labeled organism-specific 16S rDNA probe. The single cell is then placed in a medium known to enrich that sequence. The medium is found by trial and error. The authors of the paper identified 75 different media which may be tried for that purpose. Since the diagnostic 16S rDNA sequence for the metaphilic organisms is set forth below, it is believed that the organism can be cultured from Amazonian soil using the diagnostic rDNA P36 sequence.

The name of "metathermophiles" is here proposed for this new group of microorganisms characterized by the presence of P36 or closely homologous sequence. The organisms are termed a group since it is not yet known into which domain the organisms may be classified, or whether a new domain will be needed. Phylogenic classifications of novel organisms such as this require extensive study and consideration before they are fully accepted by taxonomic authorities. It appears that the P36 organisms may be among the first organisms that evolved after the thermophiles but before the evolution of oxygen evolving bacteria. This evolutionary conclusion is, of course, tentative and will require additional study.

EXAMPLES

Soils were obtained from zero to 10 centimeters in depth from sites at the Fazenda Vitoria, Paragominas, Brazil. DNA was extracted from the soil samples and clone libraries were constructed from the DNA extracted by methods described by Borneman et al., *Appl. Environ. Microbiol.* 62:1935–1943 (1996), except that further DNA purification was done by agarose gel isolation of all DNA fragments larger than 10 kb and rRNA gene were amplified by 30 cycles of PCR amplification. The soil rDNA sequences, along with sequences representing the major bacterial taxa, were aligned utilizing the PILEUP (Genetics Computer Group) computer software. A pairwise distance matrix and phylogenetic tree were performed on the rRNA sequences isolated calculated by the Jukes-Cantor and neighbor-joining algorithms. The classification of all the resulting clones is illustrated in FIGS. 1A–1C which is a phylogenic tree generated by the computer software based on the rDNA sequences which are uncovered. Soil clones are represented by a P if they were isolated from reformed pasture and were designated by an M if they were isolated by primary forests, each designation being followed by a clone number. The names of major taxa are shown in boldface in FIGS. 1A–1C. The sequences were each approximately 500 bases in length. The clones designated M1 to M73 and P1 to P72 were assigned GenBank accession numbers U68589-U68637 and U68638-U68688, respectively.

A phylogenetic analysis of the rDNA sequences were performed. A maximum likelihood analysis of soil rDNA clones (clones P17, M17, M12, and P36) was performed by using the method designated fastDNAml 1.0 (Olsen et al., *Comput. Appl. Biosci.* 10:41–48 (1994)). These analysis used empirical base frequencies and 853 unambiguously alienable nucleotide positions. The results generated the phylogenetic map illustrated in FIG. 3. Numbers at the nodes represent the percentage of 100 bootstrap replications that support the branching pattern radiating away from the node. Bootstrap percentages less than 50% are not shown. The number of changes per sequence position at the median rate is shown on the scale bar.

Secondary structure analysis of the P36 rRNA sequence was done as described by Van de Peer et al. (1994) using the CORD program found in their database. The putative secondary structure of the partial (943 base pair) rDNA clone P36 is illustrated in FIGS. 2A–2C. In FIG. 2, the numbered arrows indicate the signature nucleotides which deviate from those otherwise known to other organisms in the bacterial domain.

Hypothetically, more DNA sequence from P36 can be obtained using the methodology of Stein et al. (1996). In this method, DNA from an environmental sample such as soil is digested with a restriction enzyme to obtain 40 kb fragments. The fragments are then cloned into a vector that accepts large pieces of inserted DNA. The ligated pieces can then be transfected into a suitable bacterial host, such as E. coli. The resulting clones would then constitute a DNA library of all microorganisms from that soil. The clones can then be hybridized with a P36 rDNA specific clone to isolate those clones which contain DNA from the P36 organism. Positively hybridizing clones can then be sequenced to obtain 40 kb or more of DNA from the P36 organism. If necessary, this approach can be extended for the eventual isolation and characterization of the entire replicon containing the rDNA gene of the P36 organism.

Until recently, culturing an organism from an environmental sample was considered to be a very difficult undertaking. However, it has recently been reported by Huber et al. that the culturing of an archaeon was accomplished from the Obsidian pool at Yellowstone National Park. Various growth conditions were used to find those circumstances in which the sequence of interest was enriched. The phylogeny of the organism suggests conditions under which the organism might thrive. In the case of Huber et al., the archaeon of interest was expected to grow under those conditions typically used by other thermophilic archaea such as anaerobic growth at high temperature, a pH of 7, and likely carbon sources. These conditions enriched for the presence of the organism of interest which was demonstrated by whole cell hybridization using a probe specific for the organism.

The positively hybridizing organism is visualized by light microscopy. The organism can then be separated from all other cells in the culture by using a strongly-focused infrared laser (also known as the optical tweezers) attached to a computercontrolled inverse microscope. The isolated organism is then cultured under the same conditions used for its enrichment.

This same methodology can be used for the metathermophilic organism described herein. Once DNA cloning is accomplished and enrichment of the organism is achieved, the organism can be studied in its purified state to determine its other characteristics and complete DNA sequence.

I claim:

1. A method of isolating microorganisms that contain a nucleotide sequence that comprises SEQ ID NO. 1, comprising the steps of isolating microorganisms from soil;

screening the isolated microorganisms to identify microorganisms having a nucleotide sequence that comprises SEQ ID NO: 1; and isolating said identified microorganisms containing a nucleotide sequence that comprises SEQ ID NO: 1.

2. A method as claimed in claim 1 wherein the soil is from the Amazon region of South America.

* * * * *